United States Patent [19]

Sims et al.

[11] Patent Number: 4,994,180
[45] Date of Patent: Feb. 19, 1991

[54] SOLVENT HANDLING SYSTEM

[75] Inventors: Carl W. Sims, St. Paul; Louis R. Hudoba, Fridley, both of Minn.

[73] Assignee: Systec, Inc., Minneapolis, Minn.

[21] Appl. No.: 473,840

[22] Filed: Feb. 1, 1990

[51] Int. Cl.⁵ ............................................. B01D 15/08
[52] U.S. Cl. ............................... 210/198.2; 210/101; 55/386; 222/387; 222/399; 222/464; 137/512; 137/883
[58] Field of Search ............... 210/198.2, 658, 659, 210/107; 55/67, 386; 137/512, 883, 884; 222/144.5, 399, 464, 387

[56] References Cited

U.S. PATENT DOCUMENTS

| | | | |
|---|---|---|---|
| 2,083,964 | 6/1937 | Schulz | 222/464 |
| 3,552,436 | 1/1971 | Stewart | 137/608 |
| 3,926,809 | 12/1975 | Jones | 55/386 |
| 4,116,046 | 9/1978 | Stein | 73/61.1 C |
| 4,174,811 | 11/1979 | Binder et al. | 239/308 |
| 4,364,263 | 12/1982 | Sankoorikal et al. | 73/61.1 C |
| 4,374,656 | 2/1983 | Schrenker et al. | 55/170 |
| 4,448,684 | 5/1984 | Paradis | 210/198.2 |
| 4,541,452 | 9/1985 | Paradis | 137/209 |

Primary Examiner—Richard V. Fisher
Assistant Examiner—Neil M. McCarthy
Attorney, Agent, or Firm—Haugen and Nikolai

[57] ABSTRACT

An improved solvent handling system for use with a liquid chromatograph is disclosed in which a manifold allows a source of pressurized gas to communicate with a plurality of solvent vessels. Individual check valves prevent return flow into the manifold and cross flow between the solvent vessels. A pressure equalization system is also provided for equalizing the pressure between each solvent vessel and the corresponding supply conduit. An individually manually operated vent is provided for sparging and pressure release.

10 Claims, 3 Drawing Sheets

SOLVENT HANDLING SYSTEM

BACKGROUND OF THE INVENTION

1. Field of the Invention

The present invention is generally directed to liquid solvent handling systems and, more particularly, an improved solvent pressurization distribution and sparging system for use with a high pressure liquid chromatograph.

2. Discussion of the Related Art

In recent years, high pressure liquid chromatography (HPLC) has become an increasingly important analytical tool. The systems have become increasingly sophisticated; today, an unattended analysis may involve analyzing multiple portions of a sample utilizing a variety of different solvents or analyzing a variety of samples with the same or different solvents. Such a system requires a sophisticated solvent distribution system. The solvent distribution system must be capable of the automatic metering of precise amounts of solvents and have the ability to switch from one solvent composition to another on an automated basis. Such solvent systems include a plurality of solvent containers connected by a manifold with a source of sparging gas, normally helium, which is used to remove dissolved gases from the solvent prior to use with the chromatograph and to pressurize the system. Each solvent container is also provided with an output conduit or tube which connects it with the solvent input access of the liquid chromatograph device. These systems are normally operated under positive pressure such that the solvent is forced rather than drawn out of the solvent container into the chromatograph device.

Manifolding multiple solvent containers together has enabled progress to be made in the automation of processing multiple tests on the chromatograph. It has, however, generated some important, heretofore unsolved, liquid handling problems.

Solvent handling systems of the class described now in use are typified by systems such as that illustrated in U.S. Pat. No. 4,448,684 issued May 15, 1984 to Paradis which describes a solvent pressurization system which includes delivery and sparging modes together with a venting system. One problem associated with such prior art manifolded, pressurized solvent distribution systems involves cross-contamination or the inadvertent mixing of solvents. Because the several solvent containers are manifolded together in parallel with respect to receiving sparging gas, such as helium from a common source, the contents of all of the containers have access to at least one common point. At certain times imbalances in the pressure between containers are likely to occur within the system. This produces a tendency for solvents from one or more containers to be forced or drawn up through the manifold and into one or more of the other containers under given circumstances. This may occur, for example, when a bottle or a particular solvent container is opened for refilling without the system first being depressurized. When this happens, solvent flows from a pressurized bottle to the unpressurized one by way of the manifold thus contaminating the entire distribution system.

In a related problem, the relatively high diffusion rate associated with the relatively small helium molecules reduces the supply pressure in the distribution lines and may actually cause negative pressures to occur in certain of the distribution lines when the pressure is removed from the system. The result is a lower pressure in the line than in the connected solvent vessel. This causes back flow of solvent from one or more of the containers into the manifold also resulting in complete cross contamination of the system.

High pressure liquid chromatography systems have traditionally utilized instrumentation designed for the chemical laboratory without reference to biocompatibility. Thus, for example, the materials used in such systems, while being relatively corrosion resistant, generally, have not been suitable for use with the types of highly corrosive mobile phases typically used in biological separations. Typical mobile phases for biological separations contain concentrations of salts, acids or bases which are proven to erode stainless steel, attack seals and provide a breeding ground for microorganisms. Because they are operated under pressure, normally these systems are housed within safety enclosures to minimize damage from any solvent which might leak from one or more of the several vessels.

Instrumentation manufacturers, then, also have to address the problem of making such systems biologically compatible or inert. In addition, systems must be able to withstand the pressure and meet other physical requirements such as minimizing leakage or loss of sparging gas through container tops and vents.

Accordingly, there exists a need to construct a biocompatible solvent handling and distribution system in which cross contamination problems are eliminated. The need exists for the materials of construction to exhibit biocompatibility and for container accesses and vents to be gas-tight when closed.

SUMMARY OF THE INVENTION

By means of the present invention many problems associated with prior art pressurized manifolded solvent supply systems for liquid chromatograph equipment are solved by the provision of certain unique improvements which overcome long standing difficulties. The present invention includes a distribution system in which crossflow of solvent between manifolded bottles is eliminated as is contamination of the system by backflow of solvent into the manifold chamber. This is accomplished for both situations in which backflow is caused by discrepancies between positive pressure, as by attempting to fill a solvent bottle without depressurizing the entire system, or in situations where backflow is initiated by pressure reduction caused by the diffusion of sparging gas.

The present invention is intended to be used in a solvent handling system in which a source of pressurized gas such as helium is connected through a pressure regulator to a manifold member via an inlet passage which is open to a common chamber within the manifold. The common chamber communicates with a plurality of outlet passages which connect to individual solvent vessels. Each of the outlet passages is connected by a hollow tube to a separate one of a plurality of pressurizable solvent vessels. An additional line connects each solvent vessel with a liquid chromatography apparatus or other device designed to use the particular solvent involved. The inlet and outlet conduits pass through a seal into the liquid solvent vessel. A sparging vent is also provided above the liquid level in each of said solvent vessels to allow for depressurizing and passage of the pressurized gas for sparging.

In accordance with the solvent handling system of the invention a one-way valve or check valve is provided in each outlet passage of the manifold connecting to a solvent vessel such that when the pressure in the line connecting the pressurized solvent vessel exceeds that in the common chamber of the manifold the valve will close preventing backflow through the manifold and crossflow between containers. In addition, the solvent handling system of the invention includes a novel internal venting system associated with each of the pressurized solvent vessels to prevent backflow when the sparging gas is turned off. A minute sized, normally 0.005 inch to 0.02 inch diameter, opening is provided in the inlet line at a point above the maximum solvent height. The opening allows the pressure in the container to equalize with reduced pressure in the line without the danger of solvent creeping back up the line out of the pressurized vessel yet is of a size which does not interfere with sparging.

The present invention also contemplates improved pressurized solvent container sealing and venting systems. A special cap insert provides for the passage of inlet and outlet tubes and also includes a venting system; both are virtually helium-tight. The sealing system for the solvent container fits a conventional solvent bottle provided with a reduced diameter pouring top threaded to receive a correspondingly threaded cap. The sealing means includes a bottle cap insert molded and machined from high density polymeric material, such a high density polyethylene (HDPE), which is chemically inert to the solvent materials used, is capable of forming a tight seal with the bottle and may be machined and drilled in a manner compatible with the passage of resilient tubes and the vent of the invention. The insert is the form of a plug member having an integrally machined or molded tapered rim which acts as a tapered plug to fit and seal the inner rim of the threaded bottle top. The rim eliminates the need for additional sealing means such as O-rings and the like and cooperates with and is held in place by a threaded cap having a central opening such that the cap engages only the rim of the insert member and holds the rim of the insert member against the matching rim of the bottle in gas tight relation when screwed down. Holes are provided for resilient inlet and outlet tubes to supply the pressurizing and sparging gas into the solvent container and to allow the passage of solvent out to the liquid chromatograph or other user. Tube passages are made gas-tight by providing an opening in the cap insert slightly smaller than the outside diameter of the tube line and passing the tube through in a stretched reduced diameter form. This technique has been found to make an excellent gas-tight seal.

The cap insert vent includes a longitudinally operated vertically positioned stem mounted in an opening through the insert. The stem member has a generally cylindrical central portion flanked by at least a lower flared or enlargered diameter conical seal portion which limits the upward travel of the stem. The lower enlarged diameter conical portion forms an additional seal with the opening which is helium-tight. The upper portion of the stem portion has a hollow interior the lower end of which connects with a cross hole provided in the side. When the vertically movable stem is in the lower or inward position, the cross hole communicates with the interior of the liquid solvent container above the liquid level so that pressure may be vented through the interior of the stem to ambient. When the stem is moved upward in a vertical direction (outward), the cross hole is moved out of communication with the interior volume of the solvent vessel and the outward expanding lower conical portion of the stem contacts the insert and effects a gas-tight closure of the vent hole. It has been found that not even helium gas defuses through this vent seal at a measurable rate. The vent operates and the seal is effected with a single moving part, the stem. The stem is provided with a relatively large easy to operate plunger-type handle which also may provide an inward stop.

DESCRIPTION OF THE PREFERRED EMBODIMENT

The ideal mobile phase handling system would be made of biologically inert material such as glass, various plastics and such compatible metal as titanium. Where materials such as plastic or polymers are used, they, of course, would be chemically inert to the broad range of highly corrosive solvents and reagents generally associated with high pressure liquid chromatography (HPLC). Other high desirable features include the ability to withstand pressurization (up to about 25 psig), a built-in degassing (sparging) capability and a filtration system to prevent passage of particulates. With respect to the materials of construction, the preferred embodiments of the present invention contemplate materials of construction compatible with the vast majority of solvents, acids and bases used in biological separations. They also contemplate (unbreakable) materials which will withstand the necessary pressures for proper operation and safety. The pressurizable liquid solvent vessels or bottles are preferably high density polyethylene (HDPE). The screw-on cap retainers are normally polypropylene with the cap insert being made of HDPE, ultra-high molecular weight polyethylene (UHMW), polypropylene or a fluorocarbon such as chlorotetrafluoroethylene (CTFE), sold as Kel-F which is a registered trademark of the 3M Company, St. Paul, Minn. The tubings and fittings are preferably tetrafluoroethylene (TFE) or tefzel (trademark of E. I. DuPont DeNemours & Co of Wilimington, Del.). The bottles and vessels are preferably heavy-walled HDPE.

Figure 1:
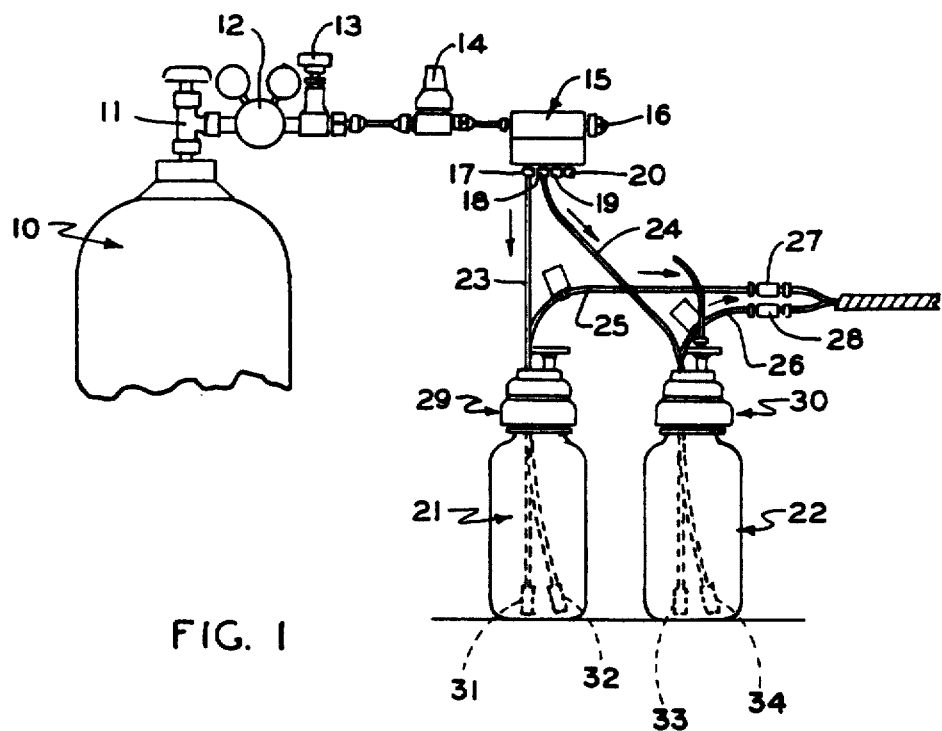
FIG. 1 depicts a typical solvent handling system in accordance with the invention illustrated by two manifolded solvent vessels.

The embodiments will now be described with reference to the drawing figures. FIG. 1 is a general illustration of a solvent handling and sparging system in accordance with the invention and includes a source of pressurized operating and sparging gas typified by the pressurized tank illustrated at 10 with valve 11, tank regulator 12, emergency shut off valve 13 and output pressure regulator 14. The manifold assembly is shown generally at 15 and in larger detail in FIGS. 3 and 3a including over pressure popoff or safety vent valve 16 and outlet passages 17–20. The solvent containing system is illustrated by a pair of high pressure vessels 21 and 22 connected respectively with outlet passages 17 and 18 of manifold 15 by conduits or tubes 23 and 24. Solvent outlet tubes are also respectively provided, illustrated by 25 and 26, which connect to the input lines of a liquid chromatograph system as at couplings 27 and 28. The solvent bottle caps in accordance with the invention are illustrated, generally by 29 and 30 and will be described in greater detail with respect to FIGS. 2, 4a and 4c. Dipper filters are further illustrated at 31–34. The inlet and outlet conduits and together with the dipper filters are shown dotted within the confines of the two solvent bottles. Whereas other bottles are not shown, it is understood that outlets to manifold 15 at 19 and 20 are normally connected to other solvent bottles or closed with gas-tight plugs.

Figure 2:
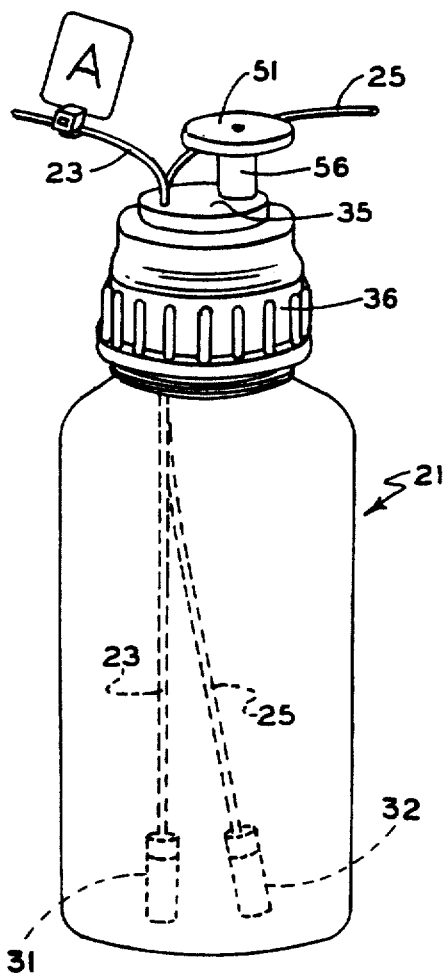
FIG. 2 depicts a typical solvent vessel and cap in accordance with the invention.
Figures 3, 4A:
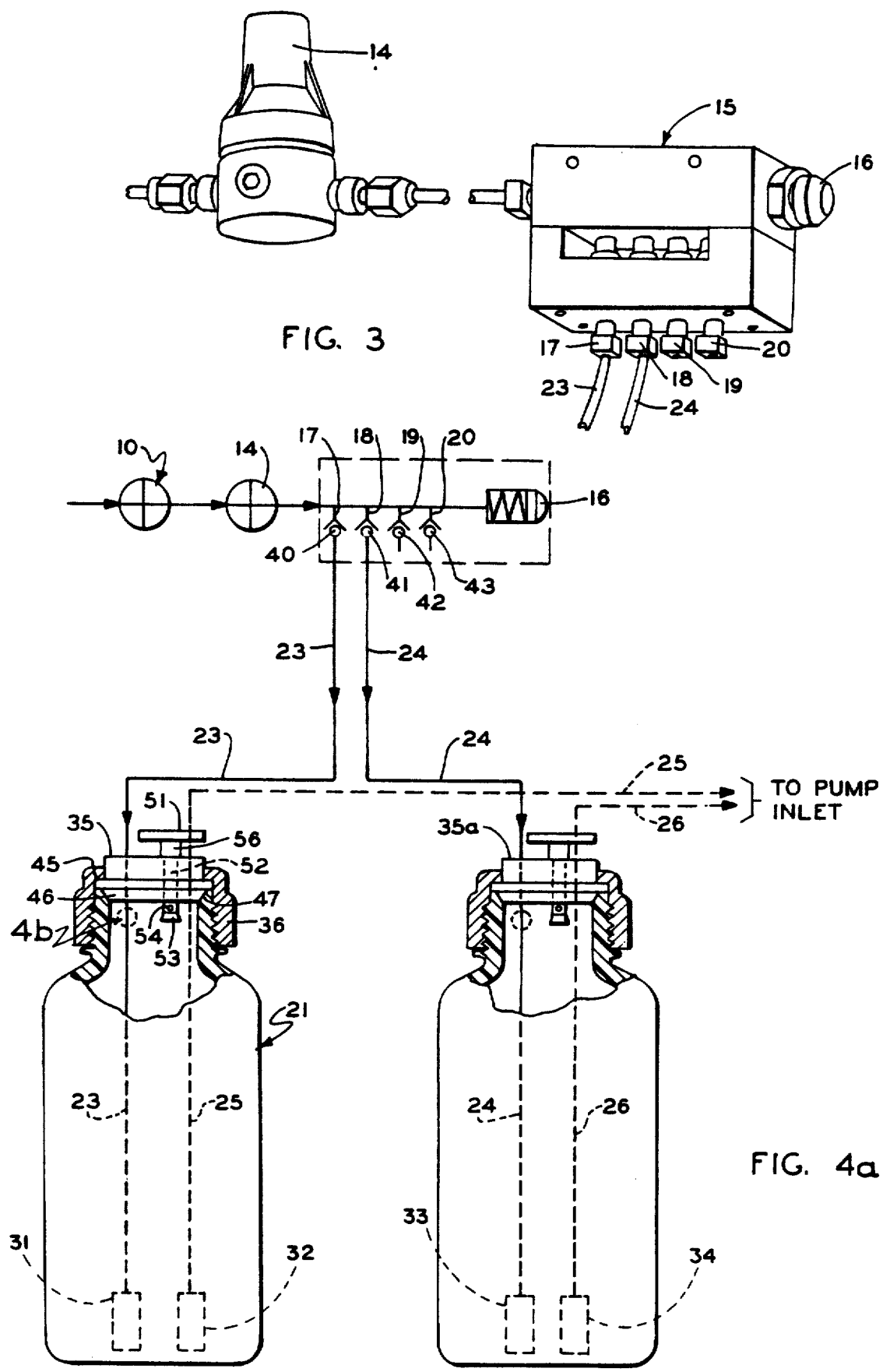
FIGS. 3 and 3a depict a portion of the sparging gas distribution system including a manifold in accordance with the invention.
FIGS. 4a–4c depict the fluid delivery system downstream of and including the manifold, partly in schematic, partly in section and including enlarged details of the vent hole and cap insert system.
Figure 4B:
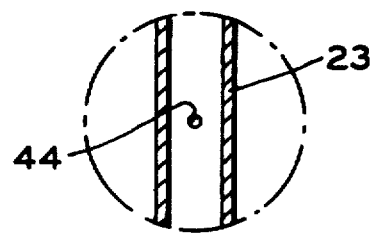
Figure 4C:
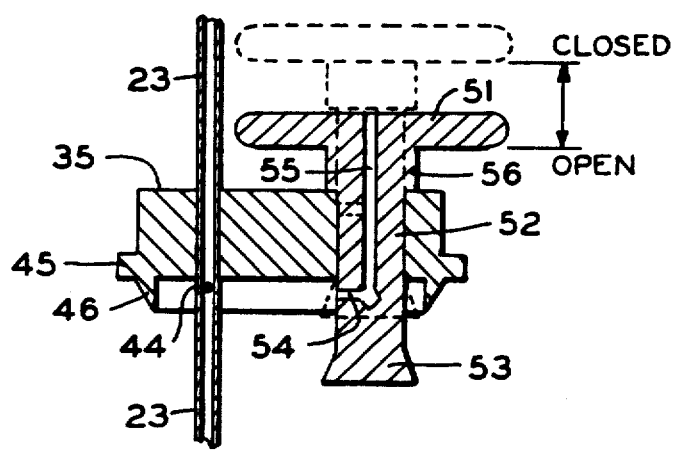

FIG. 2 is an enlarged view of one of the solvent containers 21 of FIG. 1 including vertically operated vent 56, cap insert 35 and overcap 36, these are described in greater detail with respect to FIGS. 4a and 4c.

Figure 3A:
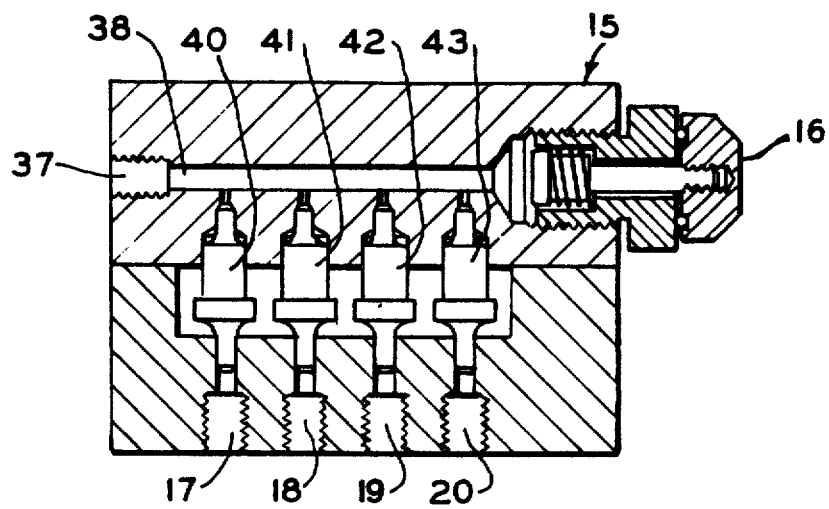

FIGS. 3 and 3a depict the system with parts broken away, of the pressure reduction regulator 14 and the manifold 15 including safety vent popoff 16 and an enlarged partial sectional view for increased clarity. It includes inlet 37 leading to common chamber 38 and check valves illustrated at 40–43.

FIG. 4a partially illustrates in schematic form, the operable details of the check valve arrangement of the manifold, bottle closure means and venting means of the invention. The four check valves 40–43 are shown each associated with an outlet line from the manifold to one of the solvent bottles. The check valves are commercially available valves manufactured of chemically resistant polymers to allow the desired unidirectioned flow. The use of an individual check valve with respect to each solvent container connection addresses and solves an important concern with respect to the design of such manifolds which distribute gas to bottles under pressure. This is the need to prevent solvent cross contamination in the form of cross flow between two or more of the bottles as a result of pressure imbalances which may be caused by any one of several reasons. This condition can occur, for example, when a bottle is opened or vented without the system first being depressurized. When this happens, solvent flows from pressurized bottles to the unpressurized one by way of the manifold, thus contaminating the entire gas distribution system. The use of these check valves solves the problem in a unique and very simple manner which automatically prevents backflow and requires no special attention, for example, when refilling a bottle. The illustrated embodiment allows up to four bottles to be simultaneously connected to the gas source. Of course, other manifolds can be used to serve any desired number of such bottles. The safety popoff valve 16 is normally one of a number of well-known valves which can be reset and which can be set to relieve pressure at a given level such as, for example, 15 psig if the normal operating pressure from regulator 14 is, for example, 7 psig.

Because of superior sparging qualities, helium is the gas normally used in such systems. The very high diffusion rate of the small molecules of the inert helium, causes any type of polymeric line utilized for the conduits as at 23 and 24 to lose helium to the atmosphere through diffusion at a rate much higher than molecules of species in air can defuse inward. If the pressure source is turned off, this diffusion will cause a lowering of pressure in the sparging line relative to the pressure in the solvent bottle or cause a vacuum to be formed if the system initially is at ambient pressure. This draws solvent from the pressurized bottle into the supply line and can even result in backflow into the manifold. Flow may be slow enough such that it will prevent proper operation of the check valve.

As best illustrated in FIG. 4b, the present invention contemplates a rather simple, novel solution to this second backflow problem. This involves the provisions of a very small bleed or vent hole or opening 44 in the inlet line which is nominally from about 0.005 to 0.02 inches in diameter and is located at a point, as illustrated in FIG. 4a, where it is above the liquid fill level line of the solvent in the solvent container so that it allows the equalization of pressure between the interior of the container and the supply line thereby preventing backflow in the system. The opening 44 is small enough not to interfere with sparging.

The unique cap system of the invention with regard to venting, closing, and allowing passage of sparging gas in and out of solvent material with respect to each solvent container will now be discussed. Typical bottle cap inserts are illustrated as at 35 and 35a in FIG. 4a and enlarged in FIG. 4c. Each insert is machined from a cast polymeric material which is chemically resistent, and has properties appropriate for the task of sealing a bottle and forming the body of a valve. The insert further includes a machined peripheral rim 45 tapered at 46 which acts as a tapered plug to fit and seal the inner rim 47 of the bottle of interest. The tapered rim of the insert 45 eliminates the need for additional sealing means such as O-rings. Typically, O-rings which are "inert" to all chemicals of interest and are capable of forming a helium leak-tight seal are very expensive. The bottle top is provided with threads which cooperate with threads of an overcap insert retaining member 36 which engages the rim 45 and threadably attaches and holds the insert to the bottle in a manner which effects a helium-tight seal. Input lines as illustrated by 23 and 24, and better shown in FIG. 2, are of a resilient material and extend through the insert member and the cap into the solvent fluid. They are suitably filtered at the ends to assure that no particulate matter gets into the chromatograph and extend close to the bottom of the containers so that almost all of the fluid in the bottle or container can be utilized. A helium-tight seal is effected between each of the resilient conduit or tubing members by providing a cylindrical passage or drilled hole in the member 35 of a diameter slightly smaller than the outside diameter of the tubing. To pass the tubing through the smaller hole in the cap, a few inches of the tubing is first heated and drawn to a diameter smaller than the hole in the cap insert. The small diameter section of the tubing is then pulled through the hole past the point at which the tubing in its normal diameter engages the hole. The tubing then attempts to return to its normal diameter thereby applying pressure against the cap sealing it helium-tight.

The final aspect of the cap to be described in accordance with the present invention involves the cap sparging vent valve. Each bottle cap has a rugged, easy to operate push-pull sparging valve which allows the user to release pressure from the bottle. The valve is helium-tight and needs no O-rings, seals or other independent sealing members which might be incompatible with the HPLC mobile phase. The valve has a relatively large handle 51 integral with a stem 52 which is manufactured such that the outer diameter of the stem 52 forms an interface with a hole drilled in the cap insert 35. As shown in FIGS. 4a and 4c, the lower portion of the stem 52 is flared outwardly at 53 and provided with a cross hole 54 which connects to the hollow upper interior 55 of the stem 52. The cross hole 54 connects the interior of the vessel with ambient through the cross hole 54 connecting with hollow line 55 when the handle 51 is depressed downward. When the handle is pulled upward, the valve then returns to the "pressurized" position in which the cross hole 54 moves into the body of the cap insert. Movement of the valve stem is limited in the upward direction by the larger diameter, conical seal section 53 machined into the stem 52. Although not shown, a corresponding taper 56 may be machined into the cap insert body to allow additional sealing with the stem at 53 when the valve is in the fully upward or "off" position. Downward movement of the valve stem is limited by the enlarged crossection 56 and 51 which is affixed to the stem by various means well within the knowledge of those skilled in the art.

It can be seen in accordance with the invention that novel and effective solutions have been provided to some ongoing problems with respect to such systems in a manner which does not materially increase the cost of the systems.

What is claimed is:

1. A solvent handling system for use with a liquid chromatograph comprising:
   a source of pressurized gas;
   means for regulating the pressures of the gas delivered from said source;
   a plurality of sealable, pressurizable solvent vessels, each of said solvent vessels having a sealing means, a gas inlet port, vent port and an outlet port;
   manifold means for simultaneously communicating said pressurized gas from said source to each of said solvent vessels, said manifold means having an inlet passage in communication with said source of said pressurized gas, a plurality of outlet passages each in corresponding communication with a gas inlet port of one of said solvent vessels, and a common chamber connecting said inlet and said plurality of outlets;
   hollow inlet conduit means connecting the gas inlet port of each said solvent vessels with a corresponding outlet passage in said manifold, said hollow conduit means being of a length sufficient to extend a distance beneath the surface of the operable solvent level associated with each said solvent vessel;
   hollow outlet conduit means to convey solvent from each of said solvent vessels to a point of use for said solvent;
   check valve means between said common chamber and each said solvent vessel for preventing flow from each of said solvent vessels into said manifold; and
   backflow prevention means associated with each solvent vessel for preventing backflow of solvent from that vessel through the corresponding hollow inlet conduit means when gas is not being delivered from the source.

2. The solvent handling system according to claim 1 in which said backflow prevention means further comprises a minute opening in said hollow conduit means above the fill level of said solvent means in each said solvent vessel.

3. The solvent handling system according to claim 1 wherein said opening is between 0.005 inches and 0.02 inches in diameter.

4. The solvent handling system according to claim 1 further characterized by vent means for venting said common chamber in said manifold if said pressure in said manifold exceeds a predetermined amount.

5. The solvent handling system according to claim 1 further characterized by a filter means at the outlet of said inlet conduit means and at the inlet of said outlet conduit means.

6. The solvent handling system according to claim 1 further characterized by vent means in each of said solvent vessels for discharging gas from said source of pressurized gas admitted to each said solvent vessels and bubbled through said solvent.

7. The solvent handling system according to claim 1 further comprising sealing means in each said solvent vessel, said sealing means comprising a bottle cap sealing insert member affixed to the bottle by a threadably attached cap which peripherally engages the cap insert.

8. The solvent handling system of claim 1 wherein the pressurized gas is helium.

9. The solvent handling system of claim 2 wherein the pressurized gas is helium.

10. The solvent handling system of claim 3 wherein the pressurized gas is helium.

* * * * *